United States Patent [19]
LaBudde

[11] Patent Number: 5,247,460
[45] Date of Patent: Sep. 21, 1993

[54] APPARATUS AND METHOD FOR IMPROVING QUALITY OF COMMINUTED MEAT PRODUCTS

[76] Inventor: Robert A. LaBudde, 824 Timberlake Dr., Virginia Beach, Va. 25464

[21] Appl. No.: 536,402

[22] Filed: Jun. 12, 1990

[51] Int. Cl.$^5$ ............................................. G06F 15/46
[52] U.S. Cl. .................................... 364/552; 426/231
[58] Field of Search ............... 364/550, 551.01, 552, 364/554, 575, 496, 502; 426/231, 246, 641

[56] References Cited

U.S. PATENT DOCUMENTS

| | | | |
|---|---|---|---|
| 3,890,825 | 6/1975 | Davis | 374/14 |
| 3,916,670 | 11/1975 | Davis et al. | 374/14 |
| 4,109,314 | 8/1978 | Meyer et al. | 426/231 X |
| 4,588,091 | 5/1986 | Wade | 364/502 X |
| 4,707,444 | 11/1987 | King, Jr. et al. | 426/231 X |
| 5,009,794 | 4/1991 | Wynn | 426/231 X |

OTHER PUBLICATIONS

Kramlich et al. *Processed Meats*, The AVI Publishing Co., Inc. pp. 158-181 and 230-311; 1973.

*Primary Examiner*—Thomas G. Black
*Assistant Examiner*—Michael Zanelli
*Attorney, Agent, or Firm*—Gene W. Arant

[57] ABSTRACT

An apparatus and method for estimating and evaluating acceptability of process variations in a blended meat processing facility. The apparatus implementing the method includes a keyboard, a data storage device, a program storage device, a calculating system and a display device. Information relating to moisture, fat, protein and Added Water are provided to the data storage by an keyboard operator. The calculator in accordance with present functions computes various factors relating to the input data and conducts tests upon the statistical validity of such computations. Providing statistical validity has been maintained, the display device then displays the outputs indicative of the variability of moisture in the blend and in one embodiment is used to control inputs and/or processing steps in the blended meat product to meet preset regulatory requirements.

1 Claim, 9 Drawing Sheets

APPARATUS AND METHOD FOR IMPROVING QUALITY OF COMMINUTED MEAT PRODUCTS

BACKGROUND AND SUMMARY OF THE INVENTION

At least a portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

1. Field of the Invention

The present invention is generally related to the meat processing industry and is specifically related to an apparatus and method for determining the source of and controlling variations in comminuted meat products.

2. Discussion of the Prior Art

The meat processing industry is regulated by the U.S. Department of Agriculture (USDA) on the basis of the chemical analysis of finished products which are marketed to the consumer. Sample lots of products are drawn on a periodic basis by USDA inspectors for chemical analysis to verify compliance with the quality control regulations. Usually, such sampling will actually be done by the meat processing company laboratory after having been certified for accuracy by the USDA.

If a meat product analysis indicates a lack of compliance to the standards, the inspector will denote the entire lot of the meat products as being "retained" which means not only that that "lot" must be reworked and cannot be shipped, but that there will be a tightened inspection in the future. Because of the cost associated with a "retained" lot, meat processors are careful to target their final product content so that violations of the USDA requirements are relatively small.

Meat processing is subject to numerous sources of variation, not found in other industries, making the problem of product consistency quite difficult. Raw meat trimmings are sold to meat processors based upon the fat content and incoming lots are routinely analyzed by the meat processor to check for the supplier's contractual compliance. Variations of fat content within ±2% of standard are considered acceptable, although this criteria is normally applied on the high fat side. The USDA also regulates "USDA Added Water" which is defined by the USDA as "moisture $-4\times$ protein." Regulation of processed meat products such as sausage, e.g., franks, bologna, luncheon meats, etc., is based upon maximum limits on the fat and "USDA Added Water" content of the consumer product.

Raw meat materials are typically blended together in a partial batch called a "preblend" or an "uncorrected" blend, which is then sampled and chemically analyzed. Based upon the analysis, the remaining material is added in adjusted amounts to "correct" the preblend to the target specification which may be a slightly conservative version of the USDA regulations governing the particular meat products. The adjusted "final" or "corrected" blend is then comminuted and passed to the stuffing department, where it is injected into casings. The product is then cooked, cooled, casings removed and packaged for shipping.

Meat processors normally conduct their own quality assurance testing to provide advance notice of possible regulatory noncompliance. Such testing normally involves chemical analysis of sampled lots for moisture, fat, protein and USDA Added Water (USDA AW). The principal sources in variation in finished product analyses result from three sources at the meat processing company. First, there is a variation in composition of the final blend or "emulsion" related to the actual blending step. Other variations in "emulsion" analysis may result from improper material use or weights, errors in assumed raw meat analysis, laboratory errors in the preblend analysis, if performed, etc.

Secondly, there are variations due to moisture loss during the cooking and holding times (this moisture loss is commonly called "shrinkage"). Additional "shrinkage" variations occur in moisture shrink loss resulting from improper smokehouse loading or schedules, faulty smokehouse equipment, abnormal holding times, etc. Thirdly, a variation is introduced in the imprecision of the laboratory analysis for moisture, fat and protein.

The laboratory analysis error can be particularly critical since protein analysis is weighted by a factor of 4 in the definition of the USDA AW. Minor variations in the protein analysis can result from insufficient mixing or comminution of the laboratory sample, the very small test weights utilized (typically 2 grams for the protein test) and variations between personnel, improper times of digestion, extraction or distillation.

Because of the large number of sources of variations encountered in meat processing, it is difficult to identify and remove assignable causes of product variation. As a result, processors must reduce their fat and USDA AW targets to provide a statistical margin of error to avoid any significant retainage. This conservative estimate of fat and USDA AW target specifications results in a "giveaway" in product analysis resulting in a 1-5% increased product cost. Therefore, it can be seen that the ability to provide product closer to a 1% cost rather than a 5% cost results in a significant cost savings and increased profit to the meat processor.

It is therefore extremely desirable in the meat processing industry to have reasonable estimates on the sizes of these three principal sources of variation in finished product analysis so that active correction action may be taken to reduce and control them. Obviously, a reduction in product chemical variability immediately results in a reduced cost of production by reducing the amount of the "giveaway." An estimation of the sizes of the three principal sources of product variation allows quick troubleshooting of problems so as to correct the area of production, i.e., blending, postblending or laboratory.

In the past, estimation of the blending variation could only be done by actual sampling and chemical analysis of samples of the final blend of meat, preferably after final comminution before stuffing into casings. The between-lots standard deviations of moisture and fat for the same product target specifications measure and provide an indication of the "uncorrected" blend variation. However, obtaining this extra sampling and analysis results in significant additional costs being incurred for this process monitoring.

In the past there has been no accepted method for determination of overall product moisture loss ("shrinkage") from the stuffing phase to the final packaging phase. The common practice has been to measure and monitor the principal component of shrink loss, that due to cooking, by weighing racked products in and out of the smokehouse. These measurements have many sources of error which limit their use for process control and include: difficulty and expense of taring (the initial zero weighing process of the racks) and identifying the racks accurately; inadvertent movement of the product from tared racks to others; loss of spray coatings of smoke treatments (which result in apparent shrinkage); lack of care by plant personnel in weighing in a busy production environment, etc. Also significant is a lack of measurement of the pre-cook and post-cook shrinkages, which can amount to several percent and can vary from batch-to-batch due to differences in holding times, etc.

Errors in the finished product laboratory analyses are difficult to detect and measure. Because of the unique lot analyses, the perishable and changeable nature of the products, small lab sample sizes, etc., it is difficult to reproduce the exact condition of a test in two different laboratories. Although laboratories may be "certified" by comparative studies with the USDA and standard methods of analysis are used, it is notorious in the industry that values obtained by the USDA laboratories, or even by outside testing laboratories, cannot in general be trusted as a definitive measure of the "true" analysis.

As a consequence, meat processing companies generally have no good idea of the exact precision and accuracy of its own laboratory. Some companies will validate their results by a between-methods comparison of moisture or fat values obtained by two different instruments or techniques. However, the effectiveness of such tests varies with the type of sample and product and generally the process of determining precision of this method is too burdensome to carry out for each and every product. It should be noted that the protein measurement analysis is particularly critical and there is currently only one accepted standard method for protein analysis. Therefore, with this measurement a "between-methods" measurement of precision cannot be attempted.

SUMMARY OF THE INVENTION

Because all meat processors perform daily analyses of their products for moisture, fat, protein and USDA AW (or some subset of these), large numbers of such analyses are accumulated over time but are used only for negative results (i.e., general indication of variable products). The present invention is to utilize the outgoing product analyses to diagnose the sources and sizes of product variation in order to permit isolation of causes of such variation so they may be removed, reduced or otherwise controlled.

It is therefore an object of the present invention to provide a method and apparatus for estimating and evaluating the acceptability of lot-to-lot process variations for a blended meat product made to a constant target or specification and providing a correction control to the processing input steps.

According to the present invention a set of good assumptions are made which render it unnecessary to obtain direct measurements of either the moisture content of the emulsion or the shrink. Standard deviations of two unknowns are estimated on the basis of historical experience. It is then possible to directly calculate a third unknown, which is a standard deviation that is critical to the accuracy of the overall process.

More specifically, there are three such standard deviations which are critical: moisture content of the blend; shrink that occurs during cooking; and laboratory error in measurement of protein content of the cooked product. The present invention makes it possible to obtain a fairly precise calculation of each of these three unknowns by first making reasonable assumptions as to the values of the other two.

In a preferred embodiment of applicant's invention, data from which it is possible to determine blend variation, moisture-loss variation and/or protein analysis variation of the blended meat product is inputted through a keyboard and stored in a data storage. These process variations in the meat product are calculated based upon the data stored in said data storage and displayed by an appropriate display means. Advantageously, applicant's invention may be conveniently implemented in a preprogrammed hand-held calculator and the method may be advantageously implemented by utilizing the calculated process variation information in a feedback loop to automatically control the variables in the desired meat processing steps.

BRIEF DESCRIPTION OF THE DRAWINGS

Various embodiments of applicant's invention may be better understood by reference to the following drawings wherein.

DETAILED DESCRIPTION OF PREFERRED EMBODIMENTS

Figure 1:
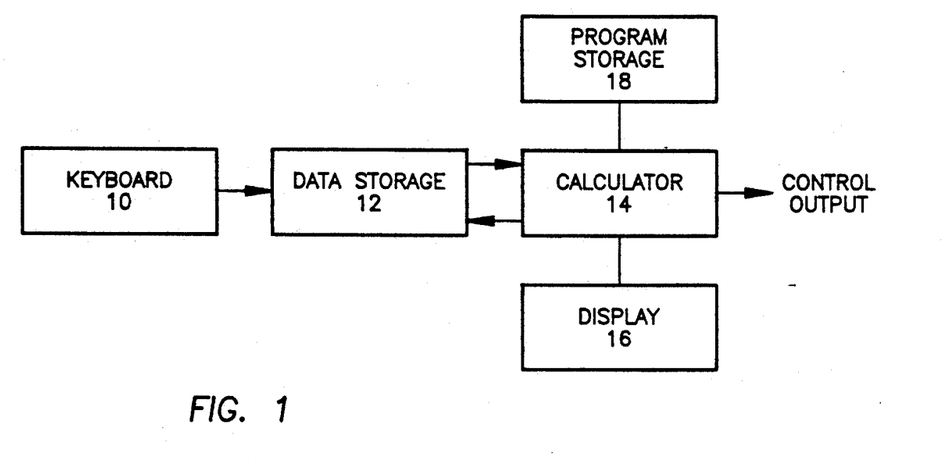
FIG. 1 comprises a block diagram of an apparatus according to applicant's invention.
Figure 2A:
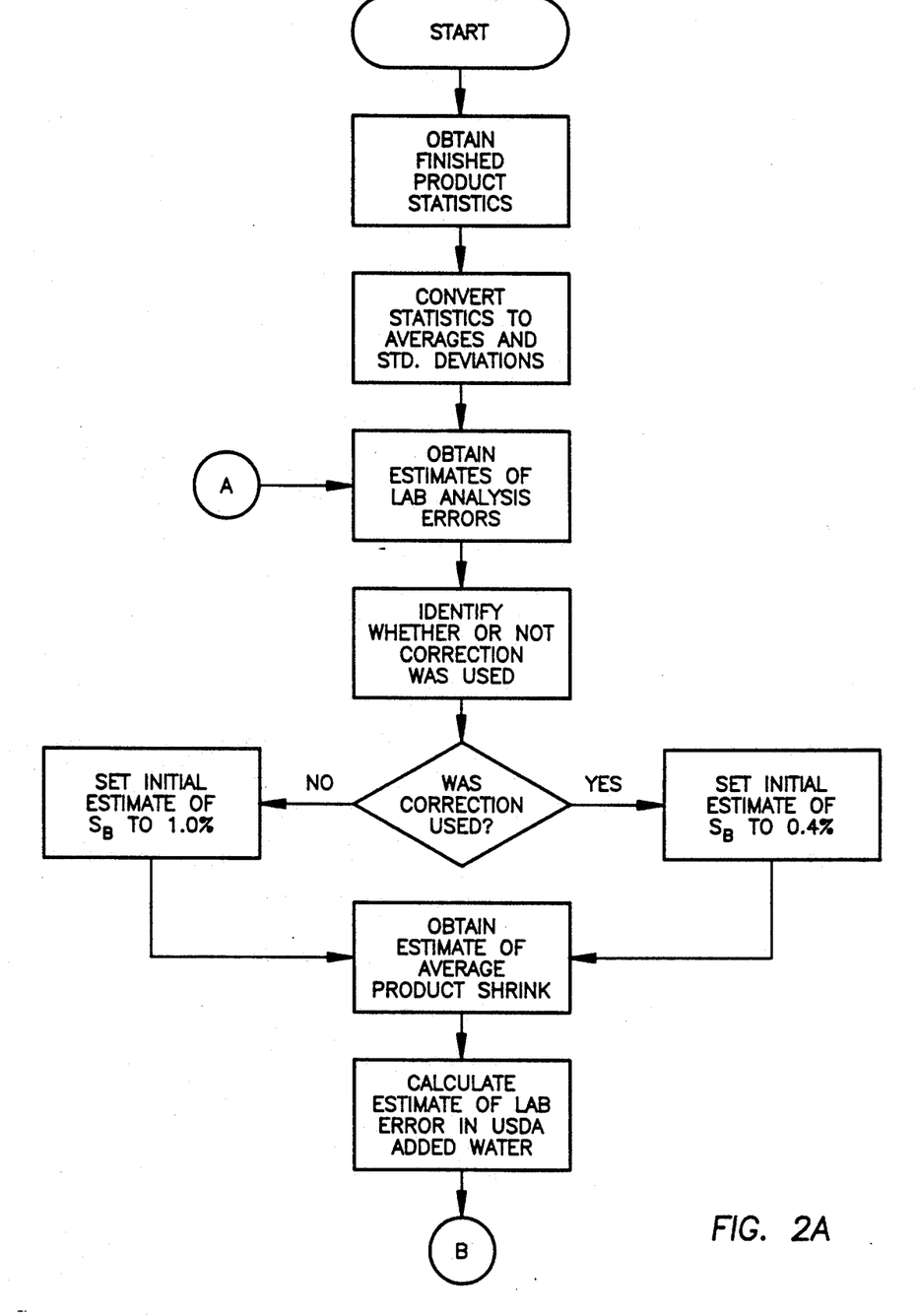
FIG. 2a through 2g are a flowchart of the steps taken in accordance with one embodiment of the present invention.
Figure 2B:
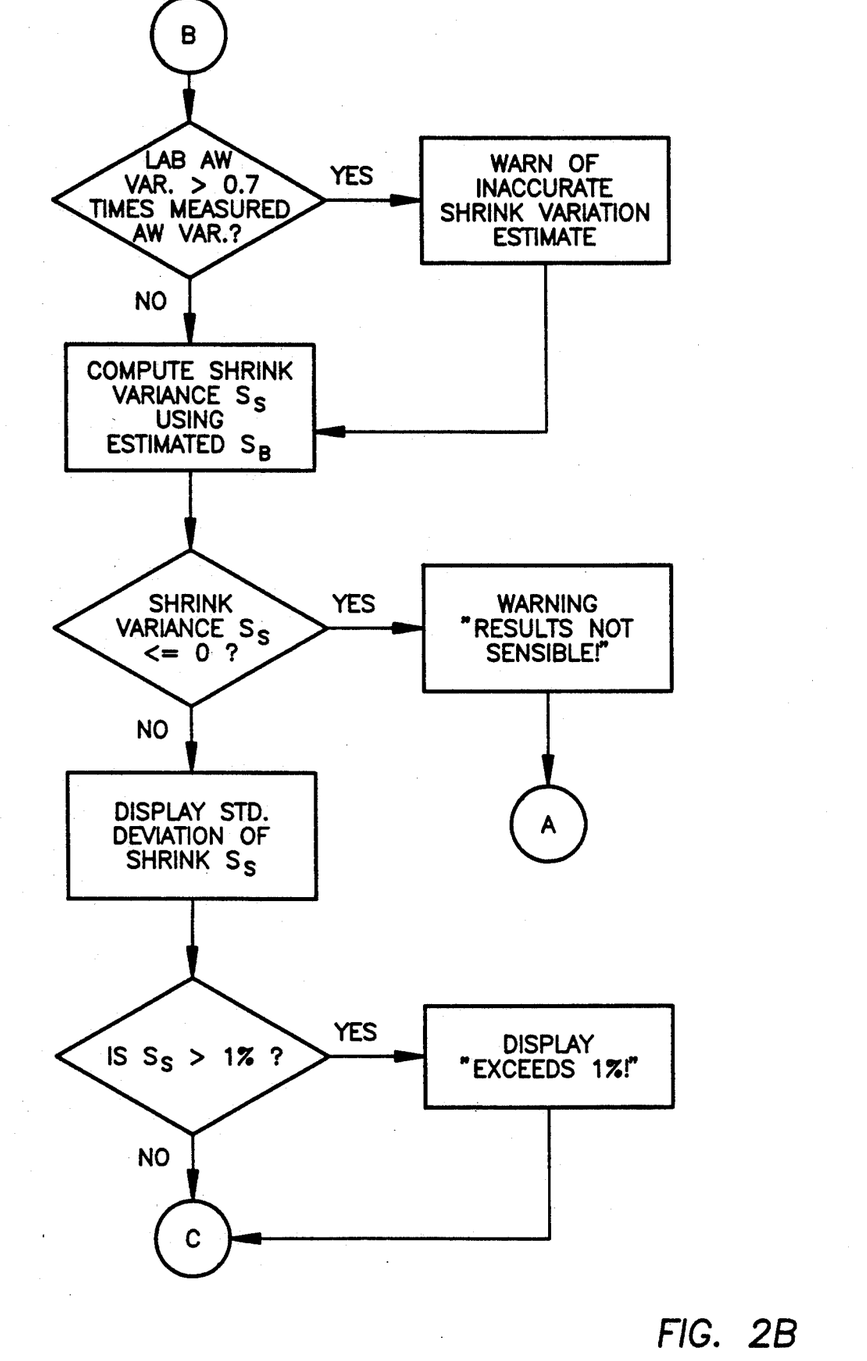
Figure 2C:
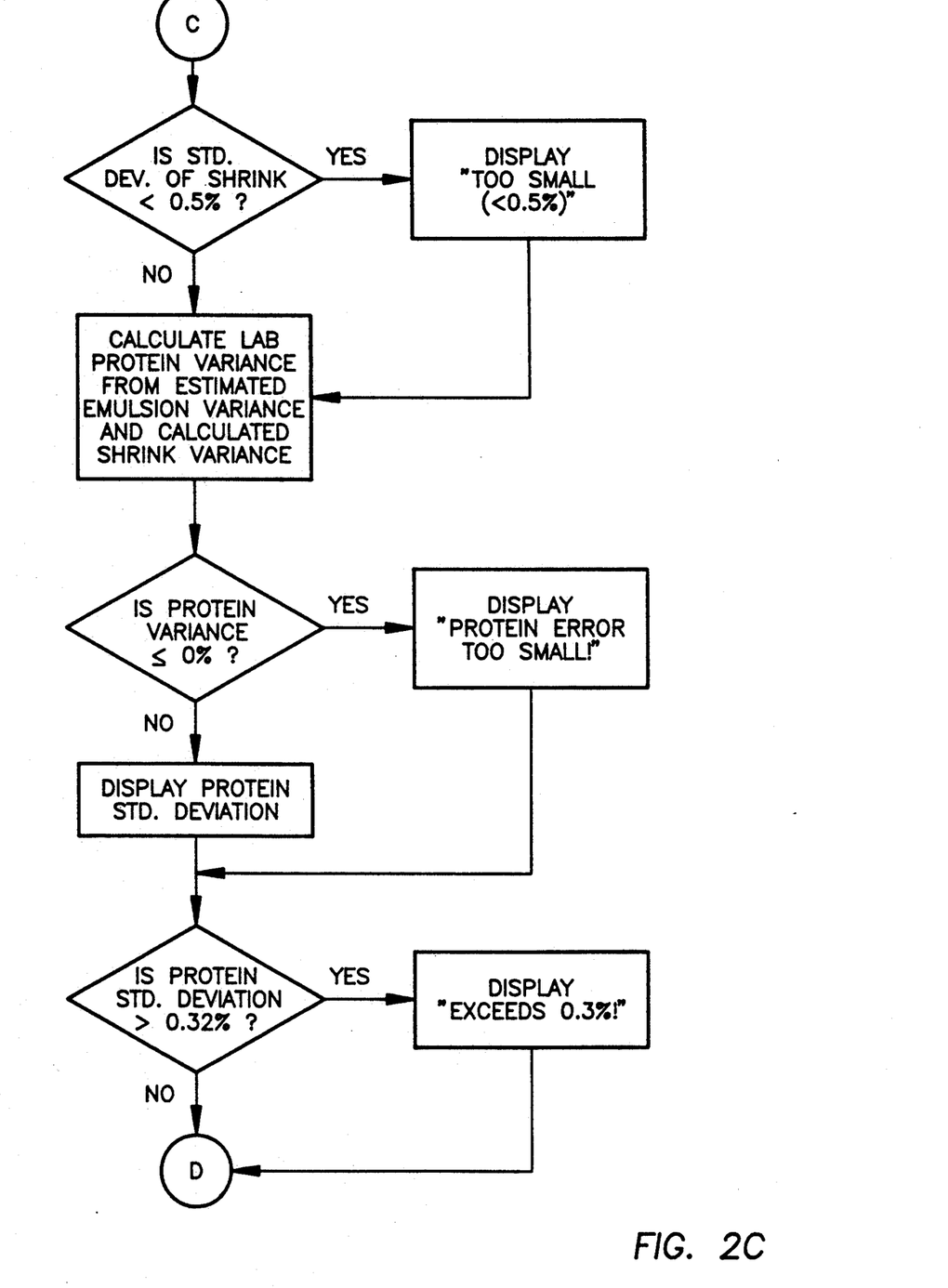
Figure 2D:
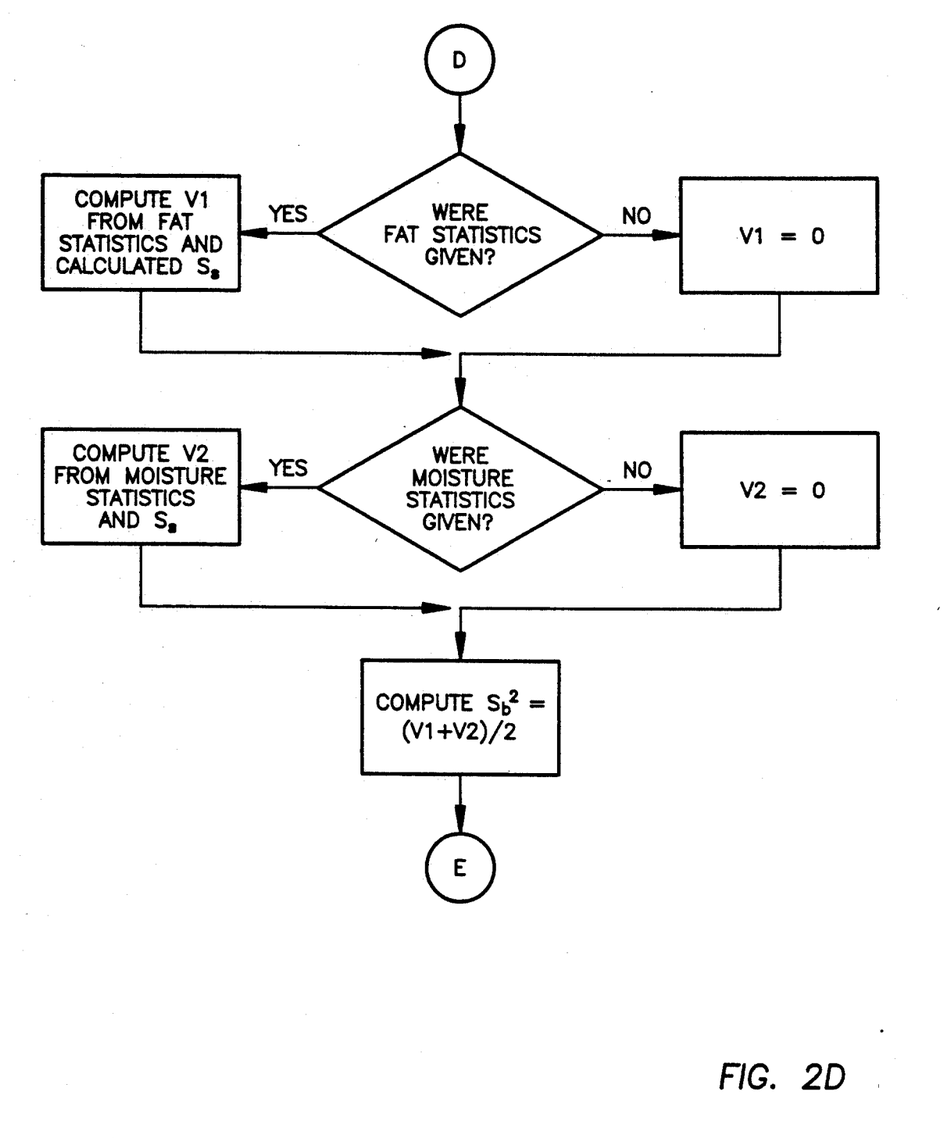
Figure 2E:
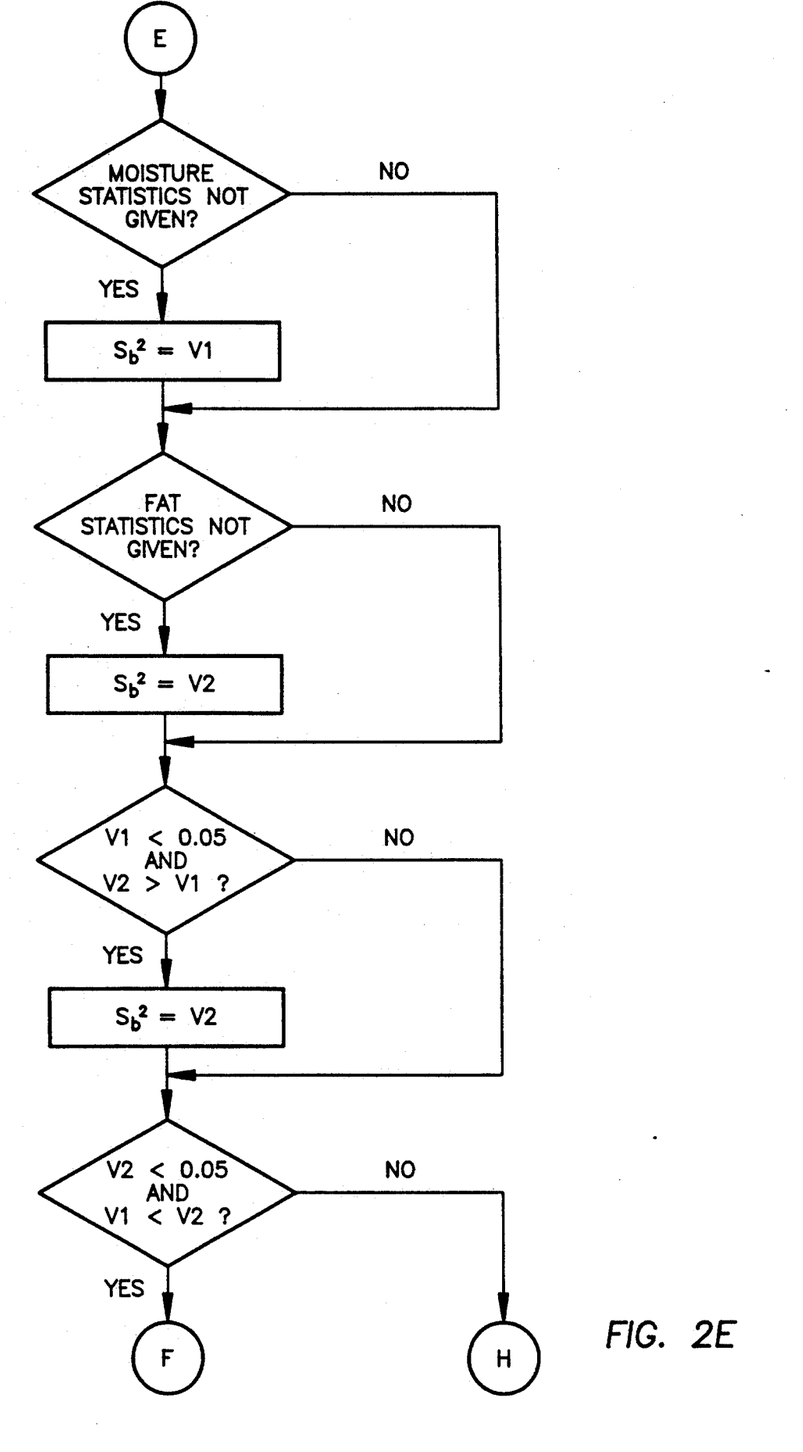
Figure 2F:
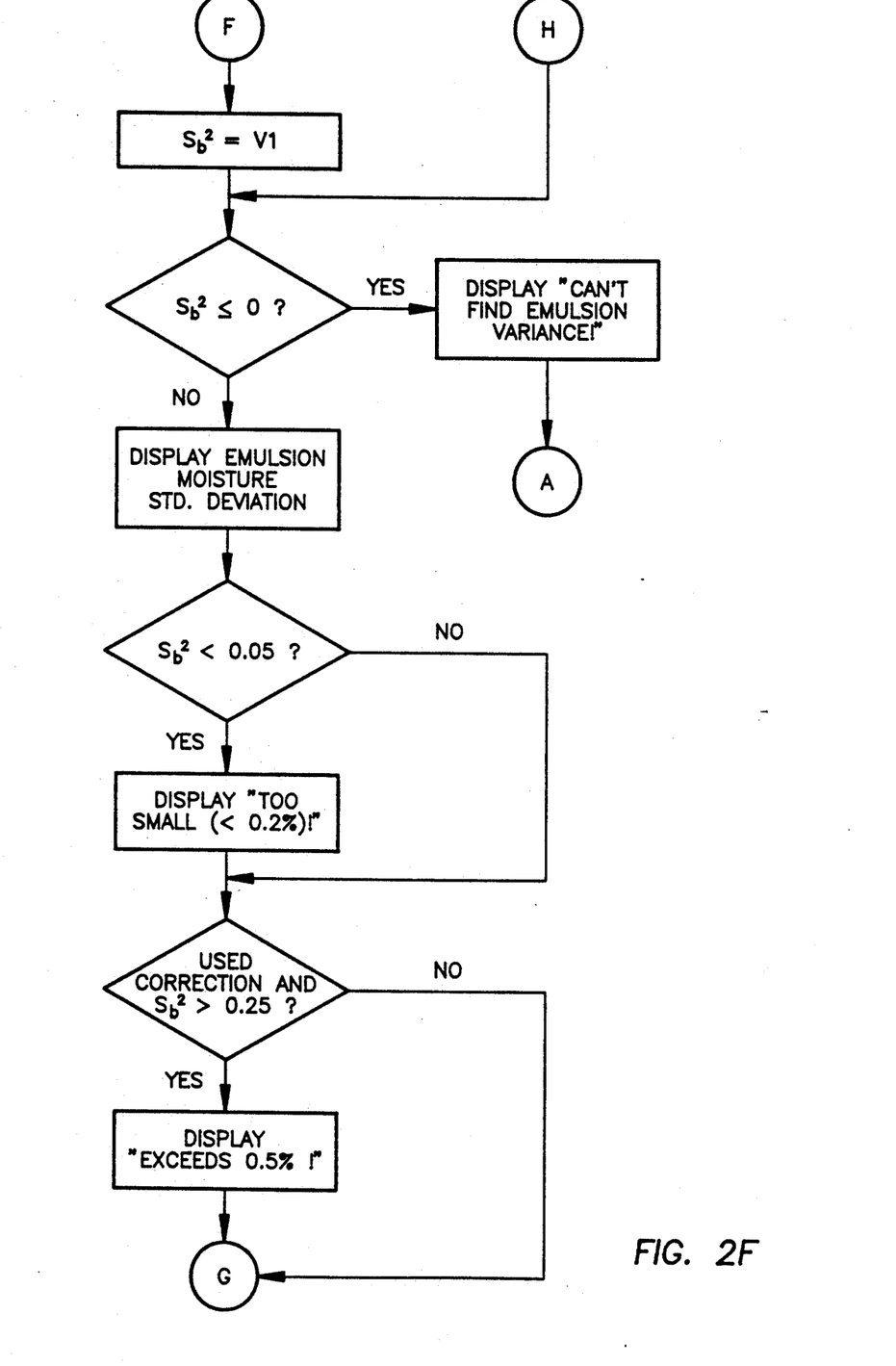
Figure 2G:
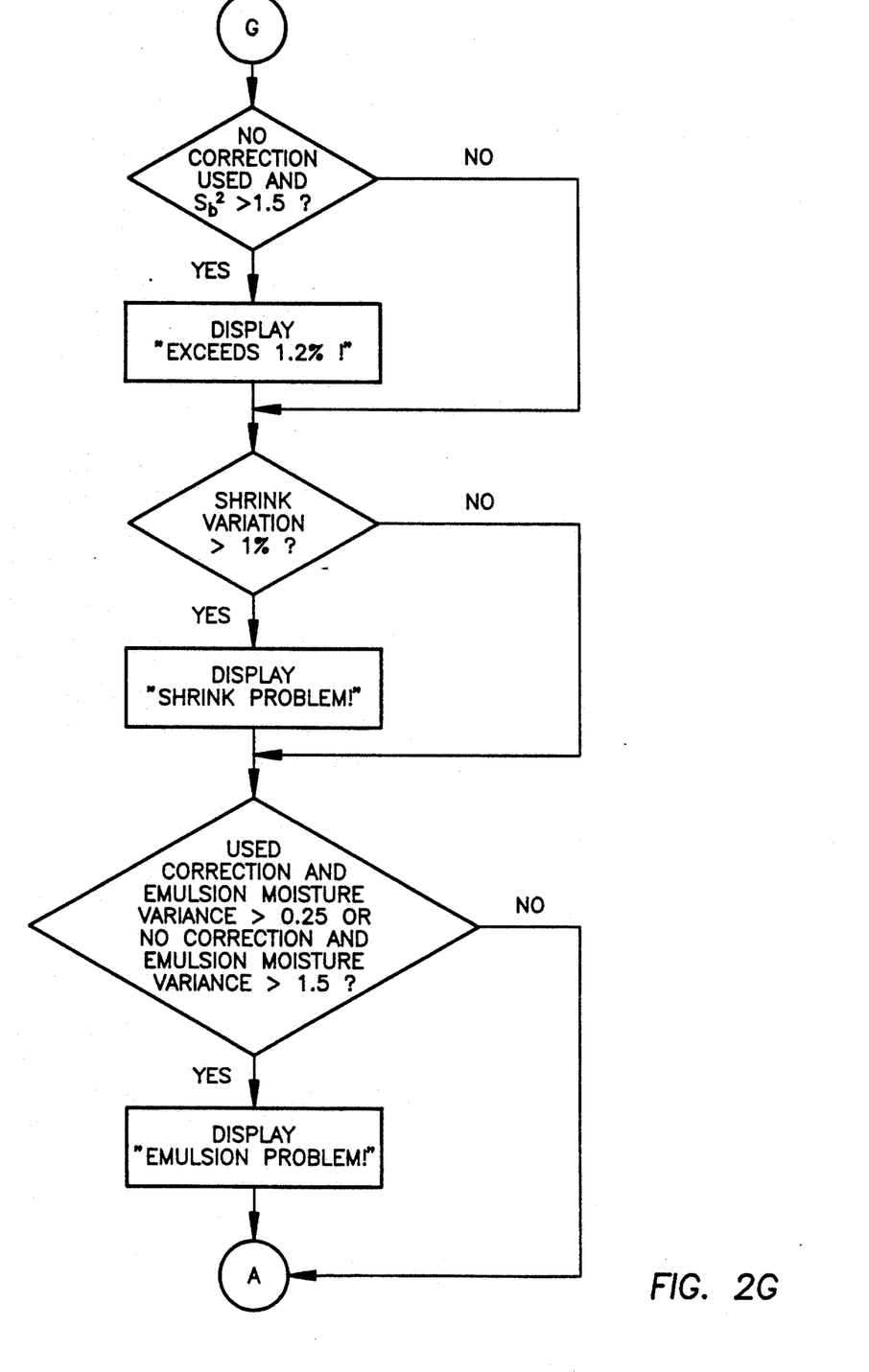

Referring now to FIG. 1, there is shown an overall block diagram of a simple embodiment of the applicant's invention. A keyboard 10 is utilized to input parameters, as measured values or estimates, which comprise information relating to blend variation, moisture-loss variation and protein analysis variation of the meat products being considered. This information is supplied to a data storage means 12 which stores the information in a Random Access Memory (RAM).

Calculator 14 is suitably programmed, for example by program storage 18, so as to access the memory of data storage 12 and process the information in an appropriate fashion so as to provide the desired process variations of the meat products which can be supplied as a control output to effect improvements in an automated meat processing system and/or provided to a display 16 in order to permit an operator to review the output and then make the desired processing step corrections.

In a preferred embodiment, the present invention is implemented with a Sharp brand hand-held PC 1350/1360 pocket computer which includes an electronically-programmable read-only memory (EPROM). The EPROM is loaded prior to operation with a suitable program, a source listing of which is attached as Appendix A hereto. In order to facilitate understanding of the operations performed and the implementation of the program, a detailed discussion of the processing steps will follow. However, to simplify this discussion, a glossary of terms is provided which includes symbols used in the specification and claims, and a cross-reference with symbols used in the program source listing and ad well as a definition of those symbols.

GLOSSARY OF SYMBOLS

| Spec/Claims | Program | Meaning |
|---|---|---|
| M | AV(MX) | Average value of moisture for lot-to-lot samples |
| F | AV(FX) | Average value of fat for lot-to-lot samples |
| P | AV(PX) | Average value of meat protein for lot-to-lot samples |
| AW | AV(AX) | Average value of Added Water for lot-to-lot samples |
| $s_M$ | S(MX) | Standard deviation of moisture for lot-to-lot samples |
| $s_F$ | S(FX) | Standard deviation of fat for lot-to-lot samples |
| $s_P$ | S(PX) | Standard deviation of protein for lot-to-lot samples |
| $s_{AW}$ | S(AX) | Standard deviation of added water for lot-to-lot samples |
| $s_m$ | SM | Estimated standard deviation of moisture analysis error |
| $s_f$ | SF | Estimated standard deviation of fat analysis error |
| $s_p$ | SP | Estimated (and later recalculated) standard deviation of protein analysis error |
| s | S | Average processing moisture shrink loss |
| $s_s$ | √VS | Standard deviation of shrink |
| $s_B$ | MM | Beginning estimate of standard deviation of moisture in final blend |
| V1 | V1 | Estimate of $s_b^2$ from fat |
| V2 | V2 | Estimate of $s_b^2$ from moisture |
| $s_b$ | √VM | Calculated estimate of standard deviation of moisture in corrected blend: Note, that $s_B$ and $s_b$ are both estimates of the same end quantity. |
| $s_{aw}$ | √X | Calculated estimate of standard deviation of Added Water determination error |

The following is a brief discussion of steps carried out to implement one embodiment of the inventive method and apparatus with reference to the flowchart disclosed in FIGS. 2a through 2g.

1. Obtain estimates of, or calculate from measurements, average moisture M, average fat F, average protein P and average Added Water AW and of standard deviations $s_M$, $s_F$, $s_P$ and $s_{AW}$, respectively. These can be inputted directly by means of the keyboard means or other data input device, or as computed from measured characteristics of outgoing product after shrinkage.

Obtain estimates of the standard deviations of the between sample laboratory error in moisture $s_m$, fat $s_f$, and protein $s_p$. If the standard deviations of $s_m$, $s_f$, $s_p$ are not known (which is usually the case), the program initially uses 0.3%, 0.4% and 0.2%, respectively, which have been determined as typical in such systems. If the final blend is a "corrected" blend, $s_B$ is set to 0.4% and if an "uncorrected" blend, $s_B$ is set to 1.0%.

2. An estimate of the average processing moisture shrink loss (s) from uncooked emulsion to the time of lab analysis is also inputted. This number is typically 3-15% for typical cooked sausage products and can be more or less for other products.

3. The terms $s_{aw}^2$ and Y are calculated in accordance with Equations 1 and 2 as follows, where the term represented by $s_{aw}^2$ is the laboratory Added Water variance and Y is a function of the measured Added Water variance (related to the standard deviation of Added Water for the samples):

$$s_{aw}^2 = s_m^2 + 16 s_p^2 \qquad \text{Eqn. 1}$$

$$Y = 0.7 \times s_{AW}^2 \qquad \text{Eqn. 2}$$

The calculations of the two terms are compared and if $s_{aw}^2$ is greater than or equal to Y, then the lab error is too large and the term "Lab Error Too Large" is displayed.

4. Shrink variance is computed based upon the following:

$$s_s^2 = \{s_{AW}^2 - s_{aw}^2 - [s_B \times 0.1/(1-s)]^2\} \times [(1-s)/(1-AW)]^2 \qquad \text{Eqn. 3}$$

In equations 3 and 4, the x indicates a multiplication function and the standard deviation of moisture in blend $s_B$ is assumed to be 0.4% if "correction is used and 1.0% if not. The term 0.1 is an estimate (viz. 1.0−4×0.275) of the contribution of the meat composition variation to Added Water variation, and the term 0.275 is an estimate of the ratio of standard deviation of protein to that of moisture due to raw meat composition variations. The factor of 0.275 is a compromise which represents with reasonable accuracy the bulk of processed meats produced in North America. The factor varies from 0.2 for comminuted chicken or turkey meat to 0.3 for chicken or turkey or beef or pork muscle meat.

Since the meat processor is aware of the species composition of his products, under ideal circumstances he could compute the weighted average by composition of the individual species' factors and use this value to replace the value 0.275 as well as 1.0−4×value to replace 0.1 in equation 3 as follows:

Value=0.20×% Comminuted Chicken+0.20×% Comminuted Turkey+0.24×% Mutton Muscle Meat+ 0.26×% Chicken Muscle Meat+0.26×% Turkey Muscle Meat+0.27×% Pork Muscle Meat+0.28×% Beef Muscle Meat where the numerical coefficients are determined by correlation analysis of measured chemical content of the meat, and the % compositions are of meat protein (ideally) or simply of meat in the blend. Generally the difference from the value 0.275 will not be significant except possibly in the case that all of the meat is from comminuted poultry.

5. Determine whether the results are reasonable. If $s_s^2$ is less than zero, then the phrase "Results Not Sensible" is reported and the analysis terminates by returning to the beginning of the process. Otherwise, $s_s$ is reported and stored as the computed standard deviation of shrink.

6. $s_s$ is compared to 1% and if greater than 1% the display indicates "Exceeds 1%." This warning indicates that the cooking steps are too variable for good process control. If the standard deviation of shrink is less than 0.5%, the phrase "Too Small (less than 0.5%)" is displayed, indicating an abnormally low, and possibly incorrect, estimate of shrink variation was found.

7. Lab protein is calculated in accordance with the following equation:

$$s_p^2 = s_p^2 - s_s^2 \times [P/(1-s)]^2 - [0.275 \, s_B/(1-s)]^2 \qquad \text{Eqn. 4}$$

If $s_p^2$ is less than zero, then "Protein Error Too Small" is reported since it apparently cannot be computed accurately. If $s_p$ is greater than 0.32%, then the term "exceeds 0.3%" is reported which indicates excessive lab protein analysis error although the system continues.

8. The standard deviation of moisture in the blend ($s_b$) is computed at this point in two different manners. First, if fat statistics were not provided, the system indicates V1 (estimate of $s_b^2$ from fat) is set to zero and the standard deviation computation based upon fat information is avoided. If fat statistics were provided, then the term V1 is calculated by equation 5 as follows and stored.

$$V1 = \{s_F^2 - s_s^2 \times [F/(1-s)]^2 - s_f^2\} \times [(1-s)/1.285]^2 \quad \text{Equ. 5}$$

In equation 5, the term 1.285 is an estimate of the ratio of the standard deviation fat to that of moisture due to raw meat composition variations. The factor of 1.285 is a compromise which represents with reasonable accuracy the bulk of processed meats produced in North America. The factor varies from 1.2 for comminuted chicken or turkey meat to 1.3 for chicken or turkey or beef or pork muscle meat. Since the meat processor is aware of the species composition of his products, under ideal circumstances he could compute the weighted average by composition of the individual species' factors and use this value to replace the value 1.285 in equation 5, as follows:

> Value = 1.22 × % Comminuted Chicken + 1.22 × % Comminuted Turkey + 1.12 × % Mutton Muscle Meat + 1.26 × % Chicken Muscle Meat + 1.26 × % Turkey Muscle Meat + 1.28 × % Pork Muscle Meat + 1.29 × % Beef Muscle Meat where the numerical coefficients are determined by correlation analysis of measured chemical content of the meat, and the % compositions are of meat fat (ideally) or simply of meat in the blend. Generally the difference from the value 1.285 will not be significant except possibly in the case that all of the meat is from mutton or comminuted poultry.

9. If moisture statistics were not provided, the system sets V2 equal to zero and bypasses the estimate of standard deviation of moisture in the blend calculation based on moisture statistics. If moisture statistics are given, then the term V2 (estimate of $s_b^2$ from moisture) is calculated in accordance with equation 6 as follows:

$$V2 = \{s_M^2 - s_s^2 \times [(1-M)/(1-s)]^2 - s_m^2\} \times (1-s)^2 \quad \text{Eqn. 6}$$

10. The average of the two estimates $s_b^2$ is computed in accordance with $s_b^2 = 0.5 (V1 + V2)$. If moisture statistics were not provided, then $s_b^2$ is set to be equal to V1. If fat statistics were not given, then $s_b^2$ is set to V2. A further comparison is made to determine whether V1 is less than 0.05 and V2 is greater than V1. If so, then $s_b^2$ is set equal to V2. If not, V2 is tested to determine whether it is less than 0.05 and V2 is less than V1. If so, $s_b^2$ is set equal to V1. In any case, $s_b^2$ is then tested to be less than or equal to zero. If it is, the display system indicates "Can't Find Emulsion Variance" and the program terminates.

If $s_b^2$ is greater than zero, the standard deviation of moisture in blend ($s_b$) is displayed. If $s_b^2$ is less than 0.05, the display indicates "Too Small (less than 0.2%)", indicating an abnormally low and possibly incorrect estimate. If $s_b^2$ is greater than or equal to 0.25 (or 1.5 if no correction is used) the display indicates "Exceeds 0.5%" (or "Exceeds 1.2%" if no correction is used) and, if not, the program continues. As a "preblend" may or may not be used, there will or will not be a correction adjustment in the final blend.

The shrink variation $s_s^2$ is then tested to be greater than 1%. If it is, then display "Shrink Problem".

If a correction is used and $s_b^2$ is greater than 0.25 or if no correction was used and $s_b^2$ is greater than 1.5, the display will indicate "Emulsion Problem". If neither of these conditions is met, the program terminates.

It is noted that although Added Water as defined by the USDA is moisture minus 4×protein, a different definition (i.e., coefficient of the multiplier for protein) of from 3.3 to 4.0 would give usable results (this would provide a coefficient of from −0.1 to +0.1 in the formula for $s_s$). The ideal definition of Added Water would be in the range of 3.5 to 3.7 (nominal 3.6) which would cause the coefficient of $s_B$ in $s_s$ to change from 0.1 to near zero, totally decoupling the two sources of variation in the equation. However, the factor of 0.1 is so small, it effectively performs the same function (less than 1% contribution).

It should also be noted that the standard deviation of fat in the meat product after blending but before shrinkage might also have to be calculated as 1.285 $s_b$. However, $s_b$ directly is usually a preferable process control variable.

It can be seen from the above that while the standard deviation of moisture loss from shrinkage ($s_s$) is calculated and is then used in the derivation of V1 and V2, if this is known it can be directly inputted bypassing Equation 3 and eliminating the necessity for some of the inputs required for the $s_s$ calculation. This is true for both equations V1 and V2. Furthermore, although in a preferred embodiment of applicant's invention both V1 and V2 are calculated (if both fat and moisture are known) the invention would still be operable if only a single equation 5 or 6 is adopted, i.e., V1 or V2. In the same manner, $s_B$ could be measured and directly inputted.

Figure 3:
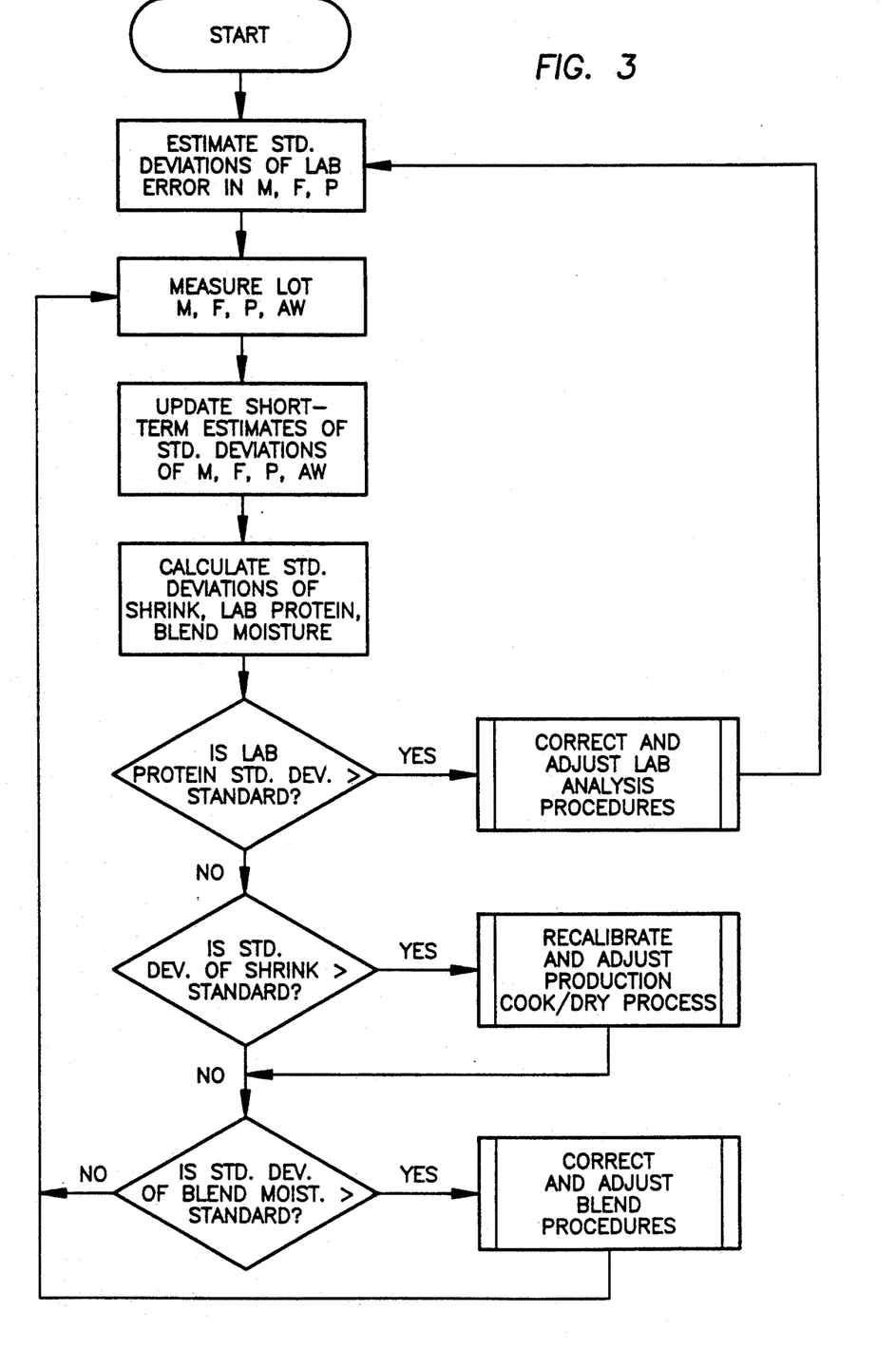
FIG. 3 is a flowchart diagram of applicant's inventive method as applied to an automated meat processing system.

Applicant's processing method can best be implemented by including a feedback loop to permit adjustment of input parameters in a meat processing system so as to automatically control meat products to a target standard. A flowchart of such a control system is illustrated in FIG. 3. While the previous description of the flowchart shown in FIGS. 2a through 2g are applicable as well, it is noted that after the three sources of variation are isolated, the input quantities are adjusted to meet the desired output standards.

It will be seen that based upon the above description and the accompanying figures, that many modifications and variations of applicant's invention will be possible. Depending upon the specific meat products used different factors and estimations will be obvious to those of ordinary skill in the art in view of this disclosure. While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

APPENDIX A

```
13000   "PROD": REM PRODUCT DIAGNOSIS 03.12.90 08.00
13010   CLEAR: DIM L$(6),X(6,20),LL$(6),AV(6),S(6),MN(6),MX(6)
13020   RESTORE 13040
13030   FOR I=1 TO 6: READ LL$(I): NEXT I
13040   DATA "MOISTURE","FAT","PROTEIN","OTHER","USDA AW","M+F+P"
13050   CLS: WAIT 0
13060   PRINT "PRODUCT DIAGNOSIS"
13070   PRINT "Which Attributes?"
13080   PRINT "M=MOIST F=FAT P=PROT"
13090   PRINT "O=OTHER A=USDA AW": WAIT
13100   INPUT "Letters in order: ";L$
13110   AX=0: MX=0: PX=0: FX=0: C$="Y"
13120   FOR I=1 TO LEN(L$)
13130   IF MID$(L$,I,1)="M" LET MX=I: L$(MX)=LL$(1)
13140   IF MID$(L$,I,1)="F" LET FX=I: L$(FX)=LL$(2)
13150   IF MID$(L$,I,1)="P" LET PX=I: L$(PX)=LL$(3)
13160   IF MID$(L$,I,1)="A" LET L$(I)=LL$(5): AX=I
13170   IF MID$(L$,I,1)<>"O" THEN 13200
13180   L$(I)=LL$(4)
13190   INPUT "LABEL FOR OTHER: ";L$(I)
13200   NEXT I
13210   CLS: WAIT 0
13220   PRINT "Stats from Where?"
13230   PRINT "1=RANGES 2=DATA 3=ENTER": WAIT
13240   INPUT "Where from? ";IS
13245   IF MX=0 OR PX=0 OR AX<>0 OR IS<>2 THEN 13260
13250   L$=L$+"a": AX=LEN(L$): L$(AX)=LL$(5)
13260   IF MX=0 OR PX=0 OR FX=0 OR IS<>2 THEN 13270
13265   L$=L$+"t": L$(LEN(L$))=LL$(6)
13270   ON IS GOSUB 34500, 34000, 13500
13280   GOSUB 34700
13290   SM=.3: SF=.4: SP=.2: SS=1
13300   IF AX=0 THEN 13210
13305   USING "#####.###"
13310   CLS: WAIT 0
13320   PRINT "Product Diagnosis"
13330   PRINT "Estimates of Lab Errors?": WAIT
13340   INPUT "Moisture: ";SM
13350   INPUT "Fat: ";SF
13360   INPUT "Protein: ";SP
13362   INPUT "Used Correction? ";C$
13364   MM=.4: IF C$<>"Y" THEN LET MM=1.0
13370   INPUT "Ave." Shrink (0-100): ";S
13375   S=.01*S
13376   X=SM 2+16*SP 2: Z=S(AX) 2
13377   IF X<.7*Z THEN 13380
13378   PRINT "Lab Error Too Large!"
13379   PRINT "Can't Find Shrink Var.!"
13380   VS=(Z-X-(MM*(1-4*.275)/(1-S)) 2)*((1-S)/(1-.01*AV(AX))) 2
13381   IF VS>0 THEN 13385
13382   PRINT ">> Results not Sensible!"
13383   GOTO 13310
13385   PRINT "Shrink Var.:",SQR(VS)
13386   IF VS>1 PRINT ">> Exceeds 1%!"
13387   IF VS<.25 PRINT ">> Too small (<0.5%)"
13388   VP=S(PX) 2-(.01*AV(PX)/(1-S)) 2*VS-(.275*MM/(1-S)) 2
13389   IF VP>0 THEN 13392
13390   PRINT ">> Protein Error Too Small!"
13391   GOTO 13393
13392   PRINT "Prot. Error:",SQR(VP)
13393   IF VP>.1 PRINT ">>Exceeds 0.3%!"
13394   V1=0: IF FX=0 THEN 13396
13395   V1=(S(FX) 2-(AV(FX)*.01/(1-S)) 2*VS-SF 2)*((1-S)/1.285) 2
13396   V2=0: IF MX=0 THEN 13400
13399   V2=(S(MX) 2-((1-.01*AV(MX))/(1-S)) 2*VS-SM 2)*(1-S) 2
13400   VM=.5*(V1+V2)
13401   IF MX=0 LET VM=V1
13402   IF FX=0 LET VM=V2
13405   IF V1<.05 AND V2>V1 LET VM=V2
13407   IF V2<.05 AND V1>V2 LET VM=V1
13410   IF VM>0 THEN 13425
13415   PRINT ">> Can't Find Emuls. Var.!"
13420   GOTO 13310
13425   PRINT "Emuls. Var.:",SQR(VM)
13430   IF VM<.05 PRINT ">> Too small (0.2%)!"
13431   IF C$="Y" AND VM>.25 PRINT ">> Exceeds 0.5%!"
13433   IF C$<>"Y" AND VM>1.5 PRINT ">> Exceeds 1.2%!"
13440   IF VS>1 PRINT "** SHRINK PROBLEM **"
13450   IF C$="Y" AND VM<=.25 THEN 13460
13455   IF C$<>"Y" AND VM<1.5 THEN 13460
13457   PRINT "** EMULSION PROBLEM **"
```

-continued

APPENDIX A

```
13460   GOTO 13310
13500   REM ENTERED
13510   FOR I=1 TO LEN(L$)
13520   CLS: WAIT 0
13530   PRINT "Enter Stats for ";L$(I)
13540   INPUT "Average: ";AV(I)
13550   INPUT "Standard Dev.: ";S(I)
13560   MN(I)=AV(I)−1.96*S(I): MX(I)=AV(I)+1.96*S(I)
13570   NEXT I
13580   RETURN
```

What is claimed is:

1. Apparatus for monitoring undesired variations in the blend ratio, the cooking process, and the laboratory testing and analysis process, in the manufacture of a comminuted meat product in successive batches by selecting a plurality of meat components each of which has its own characteristics of protein, fat, and moisture content, blending the components in a selected blend ratio to produce an emulsion, cooking the emulsion and thereby changing its moisture content to provide a cooked product, and then by a laboratory process testing and analyzing the cooked product to measure its conformance to a predetermined minimum protein content, to a predetermined maximum fat content, and to a predetermined maximum moisture content; said apparatus comprising, in combination:

(a) computer means including a microprocessor having data storage means including a random access memory, keyboard means for entering data into said data storage means, and an EPROM associated with said microprocessor for storing a program for said microprocessor;

(b) said keyboard means being adapted for entering into said data storage means an average value for each of moisture, protein, fat content, and added water of the cooked product, and also a standard deviation for each of such average values;

(c) said keyboard means being also adapted for entering into said data storage means an estimated average value of shrinkage of the cooked product;

(d) said keyboard means further being adapted for entering into said data storage means estimated standard deviations of the three variables (1) moisture content of the uncooked emulsion, (2) shrinkage of the cooked product, and (3) laboratory error in measurement of the protein content of the cooked product;

(e) computer program means controlled by said EPROM and responsive to said stored average values, standard deviations thereof, and two of said estimated standard deviations of said three variables, for calculating a standard deviation of the third one of said three variables; and (f) computer program means for comparing said calculated standard deviation with a respectively associated process control standard to provide a comparison result.

* * * * *